United States Patent
Bartholomeusz et al.

(12)

(10) Patent No.: US 7,931,907 B2
(45) Date of Patent: Apr. 26, 2011

(54) HEPATITIS B VIRUS DNA POLYMERASE AND SURFACE ANTIGEN VARIANTS AND METHODS OF USING SAME

(75) Inventors: Angeline Ingrid Bartholomeusz, Victoria (AU); Stephen Alister Locarnini, Victoria (AU); Anna Ayres, Victoria (AU); Margaret Rose Littlejohn, Victoria (AU); Geoffrey William McCaughan, New South Wales (AU); Peter William Angus, Victoria (AU)

(73) Assignees: Melbourne Health, Parkville, Victoria (AU); Austin and Repatriation Medical Centre, Heidelberg, Victoria (AU); Central Sydney Area Health Service, Camperdown (AU)

( * ) Notice: Subject to any disclaimer, the term of this patent is extended or adjusted under 35 U.S.C. 154(b) by 56 days.

(21) Appl. No.: 12/245,994

(22) Filed: Oct. 6, 2008

(65) Prior Publication Data

US 2009/0155771 A1    Jun. 18, 2009

Related U.S. Application Data

(62) Division of application No. 10/297,664, filed as application No. PCT/AU01/00690 on Jun. 8, 2001, now Pat. No. 7,431,933.

(30) Foreign Application Priority Data

Jun. 9, 2000  (AU) ...................................... PQ8109

(51) Int. Cl.
  *A61K 39/29* (2006.01)
  *A61K 39/38* (2006.01)
  *C12Q 1/70* (2006.01)

(52) U.S. Cl. .......... 424/227.1; 435/5; 435/235.1; 435/6; 424/184.1

(58) Field of Classification Search ........................ None
  See application file for complete search history.

(56) References Cited

U.S. PATENT DOCUMENTS

| | | |
|---|---|---|
| 6,555,311 B1 | 4/2003 | Locarnini et al. |
| 7,431,933 B2 | 10/2008 | Bartholomeusz |
| 2004/0005541 A1 | 1/2004 | Bartholomeusz et al. |

FOREIGN PATENT DOCUMENTS

| | | |
|---|---|---|
| WO | 98 21317 A | 5/1998 |
| WO | 99 66047 A | 12/1999 |
| WO | WO 00/28009 | 5/2000 |
| WO | 00 61758 A | 10/2000 |

OTHER PUBLICATIONS

Yeh C-T et al; "Clearance of the Original Hepatitis B Virus YMDD-Motif Mutants With Emergence of Distinct Lamivudine-Resistant Mutants During Prolonged Lamivudine Therapy"; Hepatology (2000) 31(6), 1318-1325.

Oon CJ et al; "Hepatitis B Virus Variants With Lamivudine-Related Mutations in the DNA Polymerase and the 'a' Epitope of the Surface Antigen are Sensitive to Ganciclovir"; Antiviral Research (1999) 41, 113-118.

Terrault NA et al; "Incidence and Clinical Consequences of Surface and Polymerase Gene Mutations in Liver Transplant Recipients on Hepatitis B Immunoglobulin"; Hepatology (1998) 28(2), 555-561.

Shields PL et al; (1999) "Selection of Hepatitis B Surface "Escape" Mutants During Passive Immune Prophylaxis Following Liver Transplantation: Potential Impact of Genetic Changes on Polymerase Protein Function" Gut (1999) 45, 306-309.

Aye et al, "Hepatitis B virus polymerase mutations during antiviral therapy in a patient following liver transplantation", Journal of Hepatology, 1997, vol. 26, pp. 1148-1153.

Pichoud et al, Hepatology, 1999, vol. 29, No. 1, pp. 230-237.

Bartholomeusz et al, Viral Hepatitis Reviews, 1998, vol. 4, No. 3, pp. 167-187.

Bartholomeusz et al, International Antiviral News, 1997, vol. 5, No. 8, pp. 123-124.

Gunther "Absence of mutations in the YMDD motif/B region of the hepatitis B virus polymerase in famciclovir failure" J. Hepatology, vol. 30 (1999), pp. 749-754.

Carman et al, "Vaccine-induced escape mutant of hepatitis B virus", The LANCET 1990; 336:325-329.

*Primary Examiner* — Bo Peng (74) *Attorney, Agent, or Firm* — Nixon & Vanderhye, P.C.

(57) ABSTRACT

The present invention relates generally to viral variants exhibiting reduced sensitivity to agents and in particular nucleoside analogues. More particularly, the present invention is directed to hepatitis B virus variants exhibiting complete or partial resistance to nucleoside analogues. The variants may also comprise corresponding mutations affecting immunological interactivity to viral surface components. The present invention further contemplates assays for detecting such viral variants which assays are useful in monitoring anti-viral therapeutic regimes and in developing new or modified vaccines directed against viral agents and in particular hepatitis B virus variants. The present invention also contemplates the use of the viral variants to screen for agents capable of inhibiting infection, replication and/or release of the virus.

4 Claims, 4 Drawing Sheets

Figure 1

DOMAIN A

```
421         430          440           450
SN_DLSWLSLD VSAAFYH^I_PPL HPAAMPHLL^I_V GSSGL^S_DRYVA
```

```
460              470                480              490
RLSS^T_NS^R_N^N_I*N N^Y_HQ^H_YG_R***D_NLH D_N^S_YCSR^N_QLYVS L^L_MLLY^K_QT^Y_FG^R_W
```

DOMAIN B

```
500              510              520             530
KLHL^Y_LS_AHPI^I_V LGFRK^I_LPMG^V_G GLSPFLLAQF TSAI^C_LA_S^V_MV^T^R_CR
```

DOMAIN C

```
540                  550                  560
AF^F_PHC^L_V^A_VF^S_AY MDD^V_LM^V_VLGA^K_RS_T V_GQ_EH^L_SR^E^S_FL^Y_T^A_S
```

DOMAIN D         DOMAIN E

```
570           580               590             600
V_IT_CN_SF_VLL_SD^L_VGI HLNP^N_QKTKRW GYSLNFMGY^V_II G
```

HEPATITIS B VIRUS DNA POLYMERASE AND SURFACE ANTIGEN VARIANTS AND METHODS OF USING SAME

RELATED APPLICATIONS

This is a divisional of application Ser. No. 10/297,664, filed May 12, 2003 (allowed), which is a U.S. national phase of PCT/AU01/00690, filed Jun. 8, 2001 (abandoned), which claims benefit of Australian Application No. PQ8109, filed Jun. 9, 2000, the entire contents of each of which is hereby incorporated by reference in this application.

FIELD OF THE INVENTION

The present invention relates generally to viral variants exhibiting reduced sensitivity to agents and in particular nucleoside analogues. More particularly, the present invention is directed to hepatitis B virus variants exhibiting complete or partial resistance to nucleoside analogues. The variants may also comprise corresponding mutations affecting immunological interactivity to viral surface components. The present invention further contemplates assays for detecting such viral variants which assays are useful in monitoring anti-viral therapeutic regimes and in developing new or modified vaccines directed against viral agents and in particular hepatitis B virus variants. The present invention also contemplates the use of the viral variants to screen for agents capable of inhibiting infection, replication and/or release of the virus.

BACKGROUND OF THE INVENTION

Bibliographic details of the publications numerically referred to in this specification are collected at the end of the description.

Specific mutations in an amino acid sequence are represented herein as "$Xaa_1 n Xaa_2$" where $Xaa_1$ is the original amino acid residue before mutation, n is the residue number and $Xaa_2$ is the mutant amino acid. The abbreviation "Xaa" may be the three letter or single letter (i.e. "X") code. The amino acid residues for Hepatitis B virus DNA polymerase are numbered with the residue methionine in the motif Tyr Met Asp Asp (YMDD) being residue number 550.

Figure 1:
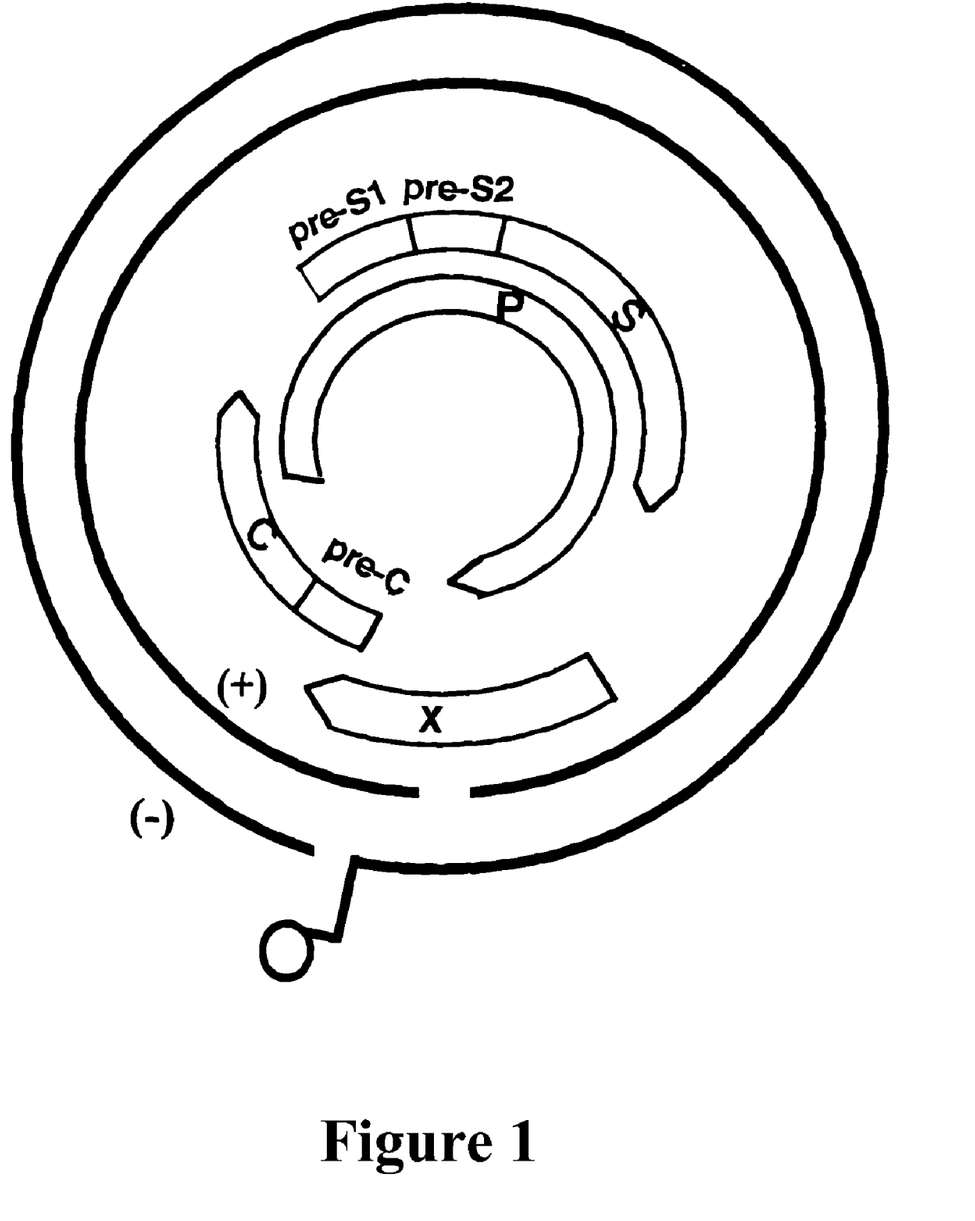
FIG. 1 is a diagrammatic representation showing the partially double stranded DNA HBV genome showing the overlapping open reading frames encoding surface (S), core (C), polymerase (P) and X gene.

Hepatitis B virus (HBV) can cause debilitating disease conditions and can lead to acute liver failure. HBV is a DNA virus which replicates via an RNA intermediate and utilizes reverse transcription in its replication strategy (1). The HBV genome is of a complex nature having a partially double stranded DNA structure with overlapping open reading frames encoding surface, core, polymerase and X genes. The complex nature of the HBV genome is represented in FIG. 1.

The presence of an HBV DNA polymerase has led to the proposition that nucleoside analogues could act as effective anti-viral agents. Examples of nucleoside analogues currently being tested are penciclovir and its oral form famciclovir [FAM] (2, 3, 4, 5) and larnivudine [LAM] (6,7). Adefovir has also been shown to have effective anti-HBV activity in vitro.

Hepatitis, due to hepatitis B virus (HBV) reactivation, is a major cause of morbidity and mortality in hepatitis B surface antigen positive (HBsAg+) patients undergoing bone marrow transplantation (BMT) (8-10). The underlying pathogenesis is related to the intense immunosuppression, during cytotoxic or immunosuppressive therapy, which enhances viral replication with a consequent increase in hepatocyte infection. Subsequent reconstitution with donors stem cells, together with the tapering down of the anti-graft-versus-host immuno suppressive agents, restore the immune function. This results in rapid destruction of infected hepatocytes (11). The outcome of allogeneic BMT is also affected by the HBV status of the donor (11). In fact, it has been shown that serological clearance of HBsAg in HBsAg+ recipients after allogeneic BMT was associated with engraftment of hepatitis B surface antibody (anti-HBs) and hepatitis B core antibody (anti-HBc) positive marrow (12-17).

As stated above, FAM is the oral prodrug of penciclovir [9-(4-hydroxy-3-hydroxymethylbut-1-yl) guanine; BRL 39123], which was shown to inhibit hepadnavirus replication in both in vitro and in vivo studies (18-22). Recently, FAM and LAM ((−)-β-2'-deoxy-3'-thiacytidine or 3TC) have been used successfully to prevent/treat hepatitis related to HBV reactivation on withdrawal of chemotherapy/immunosuppression (23, 24) and to prevent HBV recurrence following orthotopic liver transplantation [OLT] (25-28).

Like LAM, FAM resistance in the post-OLT setting has been identified in both immunosuppressed and immunocompetent subjects. The reported FAM polymerase mutations associated with "breakthrough" include G518E (29), V519L (30), G520C (29), P523L (30), L526M (30), L526V (31), T530S (29), V553I (32). Since the polymerase gene of HBV overlaps the envelope gene, mutations in the catalytic domain of the polymerase can affect the amino acid sequence of the envelope protein and vice versa. In particular, the genetic sequence for the neutralization domain of HBV known as the "a" determinant, which is found within the HBsAg and located between amino acids 99 and 169, actually overlaps the major catalytic regions of the viral polymerase protein and in particular domains A and B (33). In fact, V519L, V553I, G518E are associated with changes to the HBsAg of E164D, stop codon at 199 and E164K, respectively (30, 32, 33). Conversely, use of HBIG for prophylaxis against HBV recurrence after OLT was associated with variants in the HBsAg, which could have concomitant changes in the polymerase gene (34-36). In work leading up to the present invention, the inventors identified the selection of HBV variants in HBsAg positive recipients treated with FAM and/or LAM following allogeneic bone marrow transplantation and post-OLT. In addition to the unique mutations in the HBV polymerase and HBsAg selected during treatment, there were a number of amino acid changes in some HBV isolates which were consistent with a change of HBV genotype in the predominant virus population.

In accordance with the present invention, the inventors have identified variants of HBV, selected following FAM and/or LAM treatment, with mutations in the HBV DNA polymerase gene which reduce the sensitivity of HBV to this nucleoside analogue. Corresponding mutations in the surface antigen also occur. The identification of these HBV variants is important for the development of assays to monitor FAM and/or LAM resistance and/or resistance to other nucleoside analogue therapeutic regimes and to screen for agents which are useful as alternative therapeutic agents.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs:

correspond numerically to the sequence identifiers <400>1, <400>2, etc. A sequence listing is provided after the claims.

One aspect of the present invention is directed to an isolated HBV variant wherein said variant comprises a nucleotide mutation in a gene encoding a DNA polymerase resulting in at least one amino acid addition, substitution and/or deletion to said DNA polymerase and wherein said variant exhibits decreased sensitivity to FAM and/or LAM and optionally other nucleoside analogues.

Another aspect of the present invention provides an HBV variant comprising a mutation in an overlapping open reading frame in its genome wherein said mutation is in a region defined by one or more of domains F and A through E of HBV DNA polymerase and wherein said variant exhibits decreased sensitivity to FAM and/or LAM and optionally other nucleoside analogues.

Yet another aspect of the present invention provides an HBV variant comprising a mutation in the nucleotide sequence encoding a DNA polymerase resulting in an amino acid addition, substitution and/or deletion in said DNA polymerase in one or more amino acids as set forth in Formulae I and/or II:

FORMULA I
(SEQ ID NO:8)
L, $B_1$, $B_2$, D, W, G, P, C, $B_3$, $B_4$, H, C, $B_5$, H, $B_6$,

I, R, $B_7$, P, R, T, P, $B_8$, R, V, $B_9$, G, G, V, F, L,

V, D, K, N, P, H, N, T, $B_{10}$, E, S, $B_{11}$, L, $B_{12}$, V,

D, F, S, Q, F, S, R, G, $B_{13}$, $B_{14}$, $B_{15}$, V, S, W, P,

K, F, A, V, P, N, L, $B_{16}$, S, L, T, N, L, L, S* wherein:
$B_1$ is L, or R, or I
$B_2$ is E, or D
$B_3$ is T, or D, or A, or N, or Y
$B_4$ is E, or D
$B_5$ is E, or K, or Q
$B_6$ is H, or R, or N,
$B_7$ is L or T
$B_8$ is A, or S
$B_9$ is T or R
$B_{10}$ is A, or T, or S
$B_{11}$ is R, or T
$B_{12}$ is V, or G
$B_{13}$ is S, or L or T, or N, or V
$B_{14}$ is T, or S, or H, or Y
$B_{15}$ is R, or H, or K, or Q
$B_{16}$ is Q, or P;
and

FORMULA II
(SEQ ID NO:7)
S $Z_1$ L S W L S L D V S A A F Y H $Z_2$ P L H P A A M

P H L L $Z_3$ G S S G L $Z_4$ R Y V A R L S S $Z_5$ S $Z_6$ $Z_7$

X N $Z_8$ Q $Z_9$ $Z_{10}$ X X X $Z_{11}$ L H $Z_{12}$ $Z_{13}$ C S R $Z_{14}$ L

Y V S L $Z_{15}$ L L Y $Z_{16}$ T $Z_{17}$ G $Z_{18}$ K L H L $Z_{19}$ $Z_{20}$

H P I $Z_{21}$ L G F R K $Z_{22}$ P M G $Z_{23}$ G L S P F L L A

Q F T S A I $Z_{24}$ $Z_{25}$ $Z_{26}$ $Z_{27}$ $Z_{28}$ R A F $Z_{29}$ H C $Z_{30}$ $Z_{31}$ F $Z_{32}$ Y M* D D $Z_{33}$ V L G A $Z_{34}$ $Z_{35}$ $Z_{36}$ $Z_{37}$ H $Z_{38}$ E $Z_{39}$ L $Z_{40}$ $Z_{41}$ $Z_{42}$ $Z_{43}$ $Z_{44}$ $Z_{45}$ $Z_{46}$ L L $Z_{47}$ $Z_{48}$ G I H L N P $Z_{49}$ K T K R W G Y S L N F M G Y $Z_{50}$ I G wherein:
X is any amino acid;
$Z_1$ is N or D;
$Z_2$ is I or P;
$Z_3$ is I or V;
$Z_4$ is S or D;
$Z_5$ is T or N;
$Z_6$ is R or N;
$Z_7$ is N or I;
$Z_8$ is N or Y or H;
$Z_9$ is H or Y;
$Z_{10}$ is G or R;
$Z_{11}$ is D or N;
$Z_{12}$ is D or N;
$Z_{12}$ is D or N;
$Z_{13}$ is S or Y;
$Z_{14}$ is N or Q;
$Z_{15}$ is L or M;
$Z_{16}$ is K or Q;
$Z_{17}$ is Y or F;
$Z_{18}$ is R or W;
$Z_{19}$ is Y or L;
$Z_{20}$ is S or A;
$Z_{21}$ is I or V;
$Z_{22}$ is I or L;
$Z_{23}$ is V or G;
$Z_{24}$ is C or L;
$Z_{25}$ is A or S;
$Z_{26}$ is V or M;
$Z_{27}$ is V or T;
$Z_{28}$ is R or C;
$Z_{29}$ is F or P;
$Z_{30}$ is L or V;
$Z_{31}$ is A or V;
$Z_{32}$ is S or A;
$Z_{33}$ is V or L or M;
$Z_{34}$ is K or R;
$Z_{35}$ is S or T;
$Z_{36}$ is V or G;
$Z_{37}$ is Q or E;
$Z_{38}$ is L or S or R;
$Z_{39}$ is S or F;
$Z_{40}$ is F or Y;
$Z_{41}$ is T or A;
$Z_{42}$ is A or S;
$Z_{43}$ is V or I;
$Z_{44}$ is T or C;
$Z_{45}$ is N or S;
$Z_{46}$ is F or V;
$Z_{47}$ is S or D;
$Z_{48}$ is L or V;
$Z_{49}$ is N or Q;
$Z_{50}$ is V or I; and
M* is amino acid 550;
and wherein S* in Formula I is designated as amino acid 420 and the first S in Formula n is designated as amino acid 421; and wherein said variant exhibits decreased sensitivity to FAM and/or LAM and optionally other nucleoside analogues.

Still another aspect of the present invention contemplates a method for determining the potential for an HBV to exhibit reduced sensitivity to FAM and/or LAM or optionally other nucleoside analogues, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and A through E or a region proximal thereto of said DNA polymerase and associated with resistance or decreased sensitivity to FAM and/or LAM wherein the presence of such a mutation is an indication of the likelihood of resistance to said FAM and/or LAM.

Yet another aspect of the present invention provides a composition comprising a variant HBV resistant to FAM and/or LAM and optionally other nucleoside analogues or an HBV surface antigen from said variant HBV or a recombinant or derivative form thereof or its chemical equivalent and one or more pharmaceutically acceptable carriers and/or diluents.

Still yet another aspect of the present invention provides a use of a variant HBV wherein said variant comprises a nucleotide mutation in a gene encoding a DNA polymerase resulting in at least one amino acid addition, substitution and/or deletion to said DNA polymerase and a decreased sensitivity to FAM and/or LAM and optionally other nucleoside analogues in the manufacture of a medicament for the treatment and/or prophylaxis of hepatitis.

Even yet another aspect, the invention contemplates a computer program product for assessing the likely usefulness of a viral variant or biological sample comprising same for determining an appropriate therapeutic protocol in a subject, said product comprising:
(1) code that receives as input $I_r$s for at least two features associated with said viral agents or biological sample comprising same, wherein said features are selected from:
  (a) the ability to exhibit resistance for reduced sensitivity to a particular compound or immunological agent;
  (b) an altered DNA polymerase from wild-type HBV;
  (c) an altered surface antigen from wild-type HBV; or
  (d) morbidity or recovery potential of a patient;
(2) code that adds said $I_r$s to provide a sum corresponding to a $P_V$ for said viral variants or biological samples; and
(3) a computer readable medium that stores the codes.

In a related aspect, the invention extends to a computer for assessing the likely usefulness of a viral variant or biological sample comprising same in a subject, wherein said computer comprises:
(1) a machine-readable data storage medium comprising a data storage material encoded with machine-readable data, wherein said machine-readable data comprise $I_r$s for at least two features associated with said viral variant or biological sample; wherein said features are selected from:—
  (a) the ability to exhibit resistance for reduced sensitivity to a particular compound or immunological agent;
  (b) an altered DNA polymerase from wild-type HBV;
  (c) an altered surface antigen from wild-type HBV; or
  (d) morbidity or recovery potential of a patient;
(2) a working memory for storing instructions for processing said machine-readable data;
(3) a central-processing unit coupled to said working memory and to said machine-readable data storage medium, for processing said machine readable data to provide a sum of said $I_r$s corresponding to a $P_V$ for said compound(s); and
(4) an output hardware coupled to said central processing unit, for receiving said $P_V$.

DETAILED DESCRIPTION OF THE PREFERRED EMBODIMENTS

The present invention is predicated in part on the identification and isolation of nucleoside analogue resistant variants of HBV following treatment of patients with FAM and/or LAM and optionally other nucleoside analogues. In particular, FAM and/or LAM treated patients gave rise to variants of HBV exhibiting decreased or reduced sensitivity to FAM and/or LAM. Reference herein to "decreased" or "reduced" in relation to sensitivity to FAM and/or LAM includes and encompasses a complete or substantial resistance to the nucleoside analogue as well as partial resistance and includes a replication rate or replication efficiency which is more than a wild-type in the presence of a nucleoside analogue. In one aspect, this is conveniently measured by an increase in viral load to a level similar or greater than pre-treatment levels.

Accordingly, one aspect of the present invention is directed to an isolated HBV variant wherein said variant comprises a nucleotide mutation in a gene encoding a DNA polymerase resulting in at least one amino acid addition, substitution and/or deletion to said DNA polymerase and wherein said variant exhibits decreased sensitivity to FAM and/or LAM and optionally other nucleoside analogues.

In addition to a mutation in the gene encoding DNA polymerase, due to the overlapping nature of the HBV genome (FIG. 1), a corresponding mutation may also occur in the gene encoding the surface antigen (HBsAg) resulting in reduced interactivity of immunological reagents such as antibodies and immune cells to HBsAg. The reduction in the interactivity of immunological reagents to a viral surface component generally includes the absence of immunological memory to recognize or substantially recognize the viral surface component. The present invention extends, therefore, to an HBV variant exhibiting decreased sensitivity to FAM and/or LAM and reduced interactivity of an immunological reagent to HBsAg wherein the variant is selected for following FAM and/or LAM treatment:

A viral variant may, therefore, carry mutation only in the DNA polymerase or both in the DNA polymerase and the HBsAg. The term "mutation" is to be read in its broadest context and includes multiple mutations.

The present invention extends to a mutation and any domain of the HBV DNA polymerase and in particular regions F and A through E provided said mutation leads to decreased sensitivity to famciclovir. Region F of the HBV DNA polymerase is defined by the amino acid sequence set forth in Formula I below:

FORMULA I
L, $B_1$, $B_2$, D, W, G, P, C, $B_3$, $B_4$, H, C, $B_5$, H, $B_6$,

I, R, $B_7$, P, R, T, P, $B_8$, R, V, $B_9$, G, G, V, F, L,

V, D, K, N, P, H, N, T, $B_{10}$, E, S, $B_{11}$, L, $B_{12}$, V,

D, F, S, Q, F, S, R, G, $B_{13}$, $B_{14}$, $B_{15}$, V, S, W, P,

K, F, A, V, P, N, L, $B_{16}$, S, L, T, N, L, L, S* wherein:
$B_1$ is L, or R, or I
$B_2$ is E, or D
$B_3$ is T, or D, or A, or N, or Y
$B_4$ is E, or D
$B_5$ is E, or K, or Q
$B_6$ is H, or R, or N,
$B_7$ is I, or T
$B_8$ is A, or S
$B_9$ is T or R
$B_{10}$ is A, or T, or S
$B_{11}$ is R, or T
$B_{12}$ is V, or G
$B_{13}$ is S, or I, or T, or N, or V
$B_{14}$ is T, or S, or H, or Y
$B_{15}$ is R, or H, or K, or Q
$B_{16}$ is Q, or P;
and wherein S* is designated as amino acid 420.

In this specification, reference is particularly made to the conserved regions as defined by Poch et al. (37) as domains A to E (see also reference 38). Regions A to E are defined by the amino acid sequence set forth in Formula II below:

FORMULA II
S $Z_1$ L S W L S L D V S A A F Y H $Z_2$ P L H P A A M

P H L L $Z_3$ G S S G L $Z_4$ R Y V A R L S S $Z_5$ S $Z_6$ $Z_7$

X N $Z_8$ Q $Z_9$ $Z_{10}$ X X X $Z_{11}$ L H $Z_{12}$ $Z_{13}$ C S R $Z_{14}$ L

Y V S L $Z_{15}$ L L Y $Z_{16}$ T $Z_{17}$ G $Z_{18}$ K L H L $Z_{19}$ $Z_{20}$

H P I $Z_{21}$ L G F R K $Z_{22}$ P M G $Z_{23}$ G L S P F L L A

Q F T S A I $Z_{24}$ $Z_{25}$ $Z_{26}$ $Z_{27}$ $Z_{28}$ R A F $Z_{29}$ H C $Z_{30}$ $Z_{31}$ F $Z_{32}$ Y M* D D $Z_{33}$ V L G A $Z_{34}$ $Z_{35}$ $Z_{36}$ $Z_{37}$ H $Z_{38}$ E $Z_{39}$ L $Z_{40}$ $Z_{41}$ $Z_{42}$ $Z_{43}$ $Z_{44}$ $Z_{45}$ $Z_{46}$ L L $Z_{47}$ $Z_{48}$ G I H L N P $Z_{49}$ K T K R W G Y S L N F M G Y $Z_{50}$ I G wherein:
X is any amino acid;
$Z_1$ is N or D;
$Z_2$ is I or P;
$Z_3$ is I or V;
$Z_4$ is S or D;
$Z_5$ is T or N;
$Z_6$ is R or N;
$Z_7$ is N or I;
$Z_8$ is N or Y or H;
$Z_9$ is H or Y;
$Z_{10}$ is G or R;
$Z_{11}$ is D or N;
$Z_{12}$ is D or N;
$Z_{13}$ is S or Y;
$Z_{14}$ is N or Q;
$Z_{15}$ is L or M;
$Z_{16}$ is K or Q;
$Z_{17}$ is Y or F;
$Z_{18}$ is R or W;
$Z_{19}$ is Y or L;
$Z_{20}$ is S or A;
$Z_{21}$ is I or V;
$Z_{22}$ is I or L;
$Z_{23}$ is V or G;
$Z_{24}$ is C or L;
$Z_{25}$ is A or S;
$Z_{26}$ is V or M;
$Z_{27}$ is V or T;
$Z_{28}$ is R or C;
$Z_{29}$ is F or P;
$Z_{30}$ is L or V;
$Z_{31}$ is A or V;
$Z_{32}$ is S or A;
$Z_{33}$ is V or L or M;
$Z_{34}$ is K or R;
$Z_{35}$ is S or T;
$Z_{36}$ is V or G;
$Z_{37}$ is Q or E;
$Z_{38}$ is L or S or R;
$Z_{39}$ is S or F;
$Z_{40}$ is F or Y;
$Z_{41}$ is T or A;
$Z_{42}$ is A or S;
$Z_{43}$ is V or I;
$Z_{44}$ is T or C;
$Z_{45}$ is N or S;
$Z_{46}$ is F or V;
$Z_{47}$ is S or D;
$Z_{48}$ is L or V;
$Z_{49}$ is N or Q;
$Z_{50}$ is V or I; and
M* is amino acid 550;
and wherein the first S is designated as amino acid 421.

Preferably, the mutation results in an altered amino acid sequence in any one or more of domains F (41) and A through E or regions proximal thereto of the HBV DNA polymerase.

Accordingly, another aspect of the present invention provides an HBV variant comprising a mutation in an overlapping open reading frame in its genome wherein said mutation is in a region defined by one or more of domains F and A through E of HBV DNA polymerase and wherein said variant exhibits decreased sensitivity to FAM and/or LAM and optionally other nucleoside analogues.

In a related embodiment, there is provided an HBV variant comprising a mutation in the nucleotide sequence encoding a DNA polymerase resulting in an amino acid addition, substitution and/or deletion in said DNA polymerase in one or more amino acids as set forth in Formulae I and/or II:

FORMULA I
L, $B_1$, $B_2$, D, W, G, P, C, $B_3$, $B_4$, H, C, $B_5$, H, $B_6$,

I, R, $B_7$, P, R, T, P, $B_8$, R, V, $B_9$, G, G, V, F, L,

V, D, K, N, P, H, N, T, $B_{10}$, E, S, $B_{11}$, L, $B_{12}$, V,

D, F, S, Q, F, S, R, G, $B_{13}$, $B_{14}$, $B_{15}$, V, S, W, P,

K, F, A, V, P, N, L, $B_{16}$, S, L, T, N, L, L, S* wherein:
$B_1$ is L, or R, or I
$B_2$ is E, or D $B_3$ is T, or D, or A, or N, or Y
$B_4$ is E, or D
$B_5$ is E, or K, or Q
$B_6$ is H, or R, or N,
$B_7$ is L or T
$B_8$ is A, or S
$B_9$ is T or R
$B_{10}$ is A, or T, or S
$B_{11}$ is R, or T
$B_{12}$ is V, or G
$B_{13}$ is S, or I, or T, or N, or V
$B_{14}$ is T, or S, or H, or Y
$B_{15}$ is R, or F or K, or Q
$B_{16}$ is Q, or P;
and

FORMULA II
S $Z_1$ L S W L S L D V S A A F Y H $Z_2$ P L H P A A M

P H L L $Z_3$ G S S G L $Z_4$ R Y V A R L S S $Z_5$ S $Z_6$ $Z_7$

X N $Z_8$ Q $Z_9$ $Z_{10}$ X X X $Z_{11}$ L H $Z_{12}$ $Z_{13}$ C S R $Z_{14}$ L

Y V S L $Z_{15}$ L L Y $Z_{16}$ T $Z_{17}$ G $Z_{18}$ K L H L $Z_{19}$ $Z_{20}$

H P I $Z_{21}$ L G F R K $Z_{22}$ P M G $Z_{23}$ G L S P F L L A

Q F T S A I $Z_{24}$ $Z_{25}$ $Z_{26}$ $Z_{27}$ $Z_{28}$ R A F $Z_{29}$ H C $Z_{30}$ $Z_{31}$ F $Z_{32}$ Y M* D D $Z_{33}$ V L G A $Z_{34}$ $Z_{35}$ $Z_{36}$ $Z_{37}$ H $Z_{38}$ E $Z_{39}$ L $Z_{40}$ $Z_{41}$ $Z_{42}$ $Z_{43}$ $Z_{44}$ $Z_{45}$ $Z_{46}$ L L $Z_{47}$ $Z_{48}$ G I H L N P $Z_{49}$ K T K R W G Y S L N F M G Y $Z_{50}$ I G wherein:
X is any amino acid;
$Z_1$ is N or D;
$Z_2$ is I or P;
$Z_3$ is I or V;
$Z_4$ is S or D;
$Z_5$ is T or N;
$Z_6$ is R or N;
$Z_7$ is N or I;
$Z_8$ is N or Y or H;
$Z_9$ is H or Y;
$Z_{10}$ is G or R;
$Z_{11}$ is D or N;
$Z_{12}$ is D or N;
$Z_{13}$ is S or Y;
$Z_{14}$ is N or Q;
$Z_{15}$ is L or M;
$Z_{16}$ is K or Q;
$Z_{17}$ is Y or F;
$Z_{18}$ is R or W;
$Z_{19}$ is Y or L;
$Z_{20}$ is S or A;
$Z_{21}$ is I or V;
$Z_{22}$ is I or L;
$Z_{23}$ is V or G;
$Z_{24}$ is C or L;
$Z_{25}$ is A or S;
$Z_{26}$ is V or M;
$Z_{27}$ is V or T;
$Z_{28}$ is R or C;
$Z_{29}$ is F or P;
$Z_{30}$ is L or V;
$Z_{31}$ is A or V;
$Z_{32}$ is S or A;
$Z_{33}$ is V or L or M;
$Z_{34}$ is K or R;
$Z_{35}$ is S or T;
$Z_{36}$ is V or G;
$Z_{37}$ is Q or E;
$Z_{38}$ is L or S or R;
$Z_{39}$ is S or F;
$Z_{40}$ is F or Y;
$Z_{41}$ is T or A;
$Z_{42}$ is A or S;
$Z_{43}$ is V or I;
$Z_{44}$ is T or C;
$Z_{45}$ is N or S;
$Z_{46}$ is F or V;
$Z_{47}$ is S or D;
$Z_{48}$ is L or V;
$Z_{49}$ is N or Q;
$Z_{50}$ is V or I; and
M* is amino acid 550;
and wherein S* in Formula I is designated as amino acid 420 and the first S in Formula II is designated as amino acid 421; and wherein said variant exhibits decreased sensitivity to FAM and/or LAM and optionally other nucleoside analogues.

Another preferred aspect of the present invention contemplates an HBV variant comprising a mutation in the nucleotide sequence encoding HBsAg resulting in an amino acid addition, substitution and/or deletion in said HBsAg in a region corresponding to the amino acid sequence set forth in Formulae I and II wherein said variant exhibits decreased sensitivity to FAM and/or LAM and optionally other nucleoside analogues.

Preferably, the variants are in isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV.

Preferred mutations in the HBV DNA polymerase include variants selected from patients with HBV recurrence following FAM and/or LAM treatment. Nucleoside analogue treatment may occur in relation to a transplantation procedure (e.g. bone marrow transplantation (BMT) or OLT) or following treatment of patients diagnosed with hepatitis. Following selection of variants, viral loads are obtainable at levels greater than pre-treatment levels.

Preferred mutations in the HBV DNA polymerase include one or more of Q471K, Q471N, Y472Q, T474A, L478L/M, N485H, Y487Y/STOP, V/G/E488L, L493L/W, F524F/L, 1533I/V, V537I, S548G, S548S/C, N/S/H584T, N/S/H584A, H584S/L R588R/S and 1599A. The term "STOP" means a stop codon. Corresponding mutations may also occur in the surface antigen (i.e. HBsAg). Preferred HbsAg's include one or more of T118R, N131T, M133K/M, M133L C139C/G and WLS2/STOP.

The identification of the variants of the present invention permits the generation of a range of assays to detect such variants. The detection of such variants may be important in identifying resistant variants to determine the appropriate form of chemotherapy and/or to monitor vaccination protocols, develop new or modified vaccine preparations.

Accordingly, another aspect of the present invention contemplates a method for determining the potential for an HBV to exhibit reduced sensitivity to FAM and/or LAM and optionally other nucleoside analogues, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and A through E or a region proximal thereto of said DNA polymerase and associated with resistance or decreased sensitivity to FAM and/or LAM wherein the presence of such a mutation is an indication of the likelihood of resistance to said FAM and/or LAM and optionally other nucleoside analogues.

Preferably, the assay detects one or more of the following mutations in the HBV DNA polymerase: Q471K, Q471N, Y472Q, T474A, L478L/M, N485H, Y487Y/STOP, V/G/E488L, L493L/W, F524F/L, I533W, V537I, S548G, S548S/C, N/S/H584T, N/S/H584A, H584S/I, R588RVS and I599A.

The detection of HBV or its components in cells, cell lysates, cultured supernatant fluid and bodily fluid may be by any convenient means including any nucleic acid-based detection means, for example, by nucleic acid hybridization techniques or via one or more polymerase chain reactions (PCRs). The term "bodily fluid" includes any fluid derived from the blood, lymph, tissue or organ systems including serum, whole blood, biopsy and biopsy fluid, organ explants and organ suspension such as liver suspensions. The invention further encompasses the use of different assay formats of said nucleic acid-based detection means, including restriction fragment length polymorphism (RFLP), amplified fragment length polymorphism (AFLP), single-strand chain polymorphism (SSGP), amplification and mismatch detection (AMD), interspersed repetitive sequence polymerase chain reaction (IRS-PCR), inverse polymerase chain reaction (iPCR) and reverse transcription polymerase chain reaction (RT-PCR), amongst others. Other forms of detection include Northern blots, Southern blots, PCR sequencing, antibody procedures such as ELISA, Western blot and immunohistochemistry. A particularly useful assay includes the reagents and components required for immobilized oligonucleotide- or oligopeptide-mediated detection systems.

Variants may also be detected with reference to the HBsAg. Preferred HBsAg mutations include one or more of T118R, N131T, M133K/M, M133L C139C/G and W182/STOP.

Figure 2:
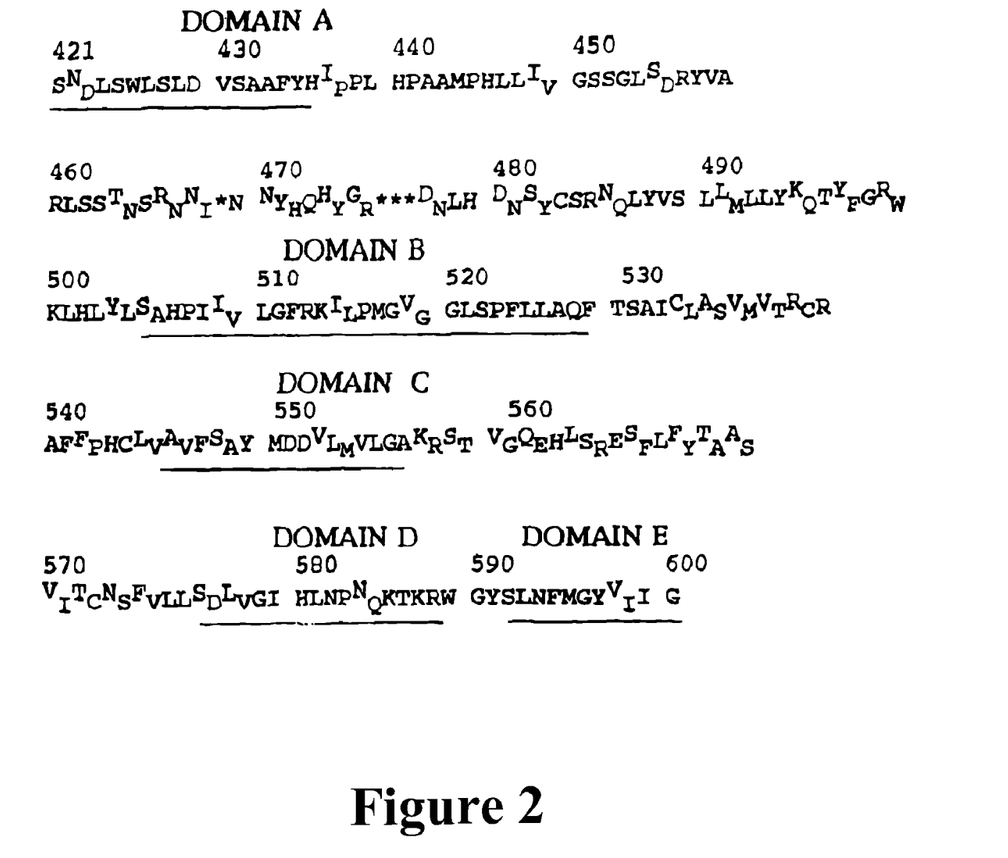
FIG. 2 is a representation showing conserved regions of domain A to E (underlined) of HBV (SEQ ID NO:7). M in YMDD is designated amino acid number 550. The symbol "*" indicates greater than three amino acid possibilities at this position of the consensus sequence. The consensus sequence defining domain A is shown in Formula I of the subject specification.

The detection of amino acid variants of DNA polymerase is conveniently accomplished by reference to the consensus amino acid sequence shown in FIG. 2 and in Formulae I and II. The polymorphisms shown represent the variations shown in various databases for active pathogenic HBV strains. Where an HBV variant comprises an amino acid different to what is represented, then such an isolate is considered a putative HBV variant having an altered DNA polymerase activity.

The present invention further contemplates agents which inhibit FAM- and/or LAM-resistant HBV variants. Such agents will be particularly useful if long term treatment by FAM and/or LAM and/or optionally other nucleoside analogues is contemplated by the clinician. The agents may be DNA or RNA or proteinaceous or non-proteinaceous chemical molecules. Natural product screening such as from plants, coral and microorganisms is also contemplated as a useful potential source of masking agents. The agents may be in isolated form or in the form of a pharmaceutical composition and may be administered sequentially or simultaneously with the nucleoside analogue.

The present invention contemplates a method for detecting an agent which exhibits inhibitory activity to an HBV with reduced sensitivity to FAM and/or LAM optionally other nucleoside analogues, said method comprising:

generating a genetic construct comprising a replication competent-effective amount of the genome from said famciclovir resistant HBV contained in or fused to an amount of a baculovirus genome effective to infect cells and then infecting said cells with said construct;

contacting said cells, before, during and/or after infection, with the agent to be tested;

culturing said cells for a time and under conditions sufficient for the HBV and optionally the further HBV to replicate, express genetic sequences and/or assemble and/or release virus or virus-like particles if resistant to said agent; and subjecting the cells, cell lysates or culture supernatant fluid to viral- or viral-component-detection means to determine whether or not the virus has replicated, expressed genetic material and/or assembled and/or been released in the presence of FAM and/or LAM.

In an alternative embodiment, the present invention provides a method for detecting an HBV agent which exhibits inhibitory activity to an HBV with reduced sensitivity to FAM and/or LAM and optionally other nucleoside analogues, said method comprising:— generating a genetic construct comprising a replication competent-effective amount of the genome from said HBV contained in or fused to an amount of a baculovirus genome effective to infect cells and then infecting said cells with said construct;

contacting said cells, before, during and/or after infection, with the agent to be tested;

culturing said cells for a time and under conditions sufficient for the HBV to replicate, express genetic sequences and/or assemble and/or release virus or virus-like particles if resistant to said agent; and subjecting the cells, cell lysates or culture supernatant fluid to viral- or viral-component-detection means to determine whether or not the virus has replicated, expressed genetic material and/or assembled and/or been released in the presence of said FAM and/or LAM.

In a further alternative embodiment of the present invention, there is provided a method for detecting an HBV agent which exhibits inhibitory activity to an HBV with reduced sensitivity to FAM and/or LAM and optionally other nucleoside analogues, said method comprising:— generating a continuous cell line comprising an infectious copy of the genome of said HBV in a replication competent effective amount such that said infectious HBV genome is stably integrated into said continuous cell line such as but not limited to 2.2.15 or AD;

contacting said cells with the agent to be tested;

culturing said cells for a time and under conditions sufficient for the HBV to replicate, express genetic sequences and/or assemble and/or release virus or virus-like particles if resistant to said agent; and subjecting the cells, cell lysates or culture supernatant fluid to viral- or viral-component-detection means to determine whether or not the virus has replicated, expressed genetic material and/or assembled and/or been released in the presence of said FAM and/or LAM.

The present invention further extends to an isolated HBsAg from the HBV variants herein described. More particularly, the present invention provides an HBsAg or a recombinant form thereof or derivative or chemical equivalent thereof. The isolated surface component and, more particularly, isolated surface antigen or its recombinant, derivative or chemical equivalents are useful in the development of biological compositions such as vaccine formulations.

Accordingly, the present invention contemplates a composition comprising a variant HBV resistant to famciclovir or an HBV surface antigen from said variant HBV or a recombinant or derivative form thereof or its chemical equivalent. The composition may be considered as a biological composition.

Generally, if an HBV is used, it is first attenuated. The biological composition according to this aspect of the present invention generally further comprises one or more pharmaceutically acceptable carriers and/or diluents.

The biological composition may comprise HBsAg or like molecule from one HBV variant or the composition may be a cocktail of HBsAgs or like molecules from a range of FAM- and/or LAM-resistant HBV variants. Similar inclusions apply where the composition comprises an HBV.

The subject invention extends to kits for assays for variant HBV resistant to FAM and/or LAM. Such kits may, for example, contain the reagents from PCR or other nucleic acid hybridization technology or reagents for immunologically based detection techniques. A particularly useful assay includes the reagents and components required for immobilized oligonucleotide- or oligopeptide-mediated detection systems.

The present invention further contemplates the use of a variant HBV resistant to FAM and/or LAM wherein said variant comprises a nucleotide mutation in a gene encoding a DNA polymerase resulting in at least one amino acid addition, substitution and/or deletion to said DNA polymerase in the manufacture of a medicament for the treatment and/or prophylaxis of hepatitis.

The present invention also provides for the use of the subject HBV variants to screen for anti-viral agents. These anti-viral agents inhibit the virus. The term "inhibit" includes antagonizing or otherwise preventing infection, replication, assembly and/or release or any intermediate step. Preferred anti-viral agents include nucleoside analogues, however, the present invention extends to non-nucleoside molecules.

Accordingly, another aspect of the present invention contemplates the use of an HBV variant resistant to FAM and/or LAM wherein said variant comprises a nucleotide mutation in a gene encoding a DNA polymerase resulting in at least one amino acid addition, substitution and/or deletion to said DNA polymerase to screen for an anti-viral agent capable of inhibiting said HBV variant.

The present invention further relates to an HBV variant comprising the mutation S548G or S548C selected following LAM treatment of a patient previously on FAM/HBIG therapy prior to transplantation of the liver. The S548G mutation occurred concurrently with L526M, M550V and Y472Q mutations as detected by sequencing of clones derived from PCR amplified product. A further mutation, S548S/C was detected in an HBV isolated from a patient treated with LAM.

An assessment of a potential viral variant is important for selection of an appropriate therapeutic protocol. Such an assessment is suitably facilitated with the assistance of a computer programmed with software, which inter alia adds index values (Iv) for at least two features associated with the viral variants to provide a potency value (Pa) corresponding to the resistance or sensitivity of a viral variant to a particular chemical compound or immunological agent. The $I_V$s can be selected from (a) the ability to exhibit resistance for reduced sensitivity to a particular compound or immunological agent; (b) an altered DNA polymerase from wild-type HBV; (c) an altered surface antigen from wild-type HBV; or (d) morbidity or recovery potential of a patient. Thus, in accordance with the present invention, $I_V$s for such features are stored in a machine-readable storage medium, which is capable of processing the data to provide a Pa for a particular viral variant or a biological specimen comprising same.

Thus, in another aspect, the invention contemplates a computer program product for assessing the likely usefulness of a viral variant or biological sample comprising same for determining an appropriate therapeutic protocol in a subject, said product comprising:

(1) code that receives as input lys for at least two features associated with said viral agents or biological sample comprising same, wherein said features are selected from:
   (a) the ability to exhibit resistance for reduced sensitivity to a particular compound or immunological agent;
   (b) an altered DNA polymerase from wild-type HBV;
   (c) an altered surface antigen from wild-type HBV; or
   (d) morbidity or recovery potential of a patient;
(2) code that adds said $I_V$s to provide a sum corresponding to a $P_V$ for said viral variants or biological samples; and
(3) a computer readable medium that stores the codes.

In a related aspect, the invention extends to a computer for assessing the likely usefulness of a viral variant or biological sample comprising same in a subject, wherein said computer comprises:

(1) a machine-readable data storage medium comprising a data storage material encoded with machine-readable data, wherein said machine-readable data comprise $I_V$s for at least two features associated with said viral variant or biological sample; wherein said features are selected from:—
   (a) the ability to exhibit resistance for reduced sensitivity to a particular compound or immunological agent;
   (b) an altered DNA polymerase from wild-type HBV;
   (c) an altered surface antigen from wild-type HBV; or
   (d) morbidity or recovery potential of a patient;
(2) a working memory for storing instructions for processing said machine-readable data;
(3) a central-processing unit coupled to said working memory and to said machine-readable data storage medium, for processing said machine readable data to provide a sum of said $I_V$s corresponding to a $P_V$ for said compound(s); and
(4) an output hardware coupled to said central processing unit, for receiving said $P_V$.

Figure 3:
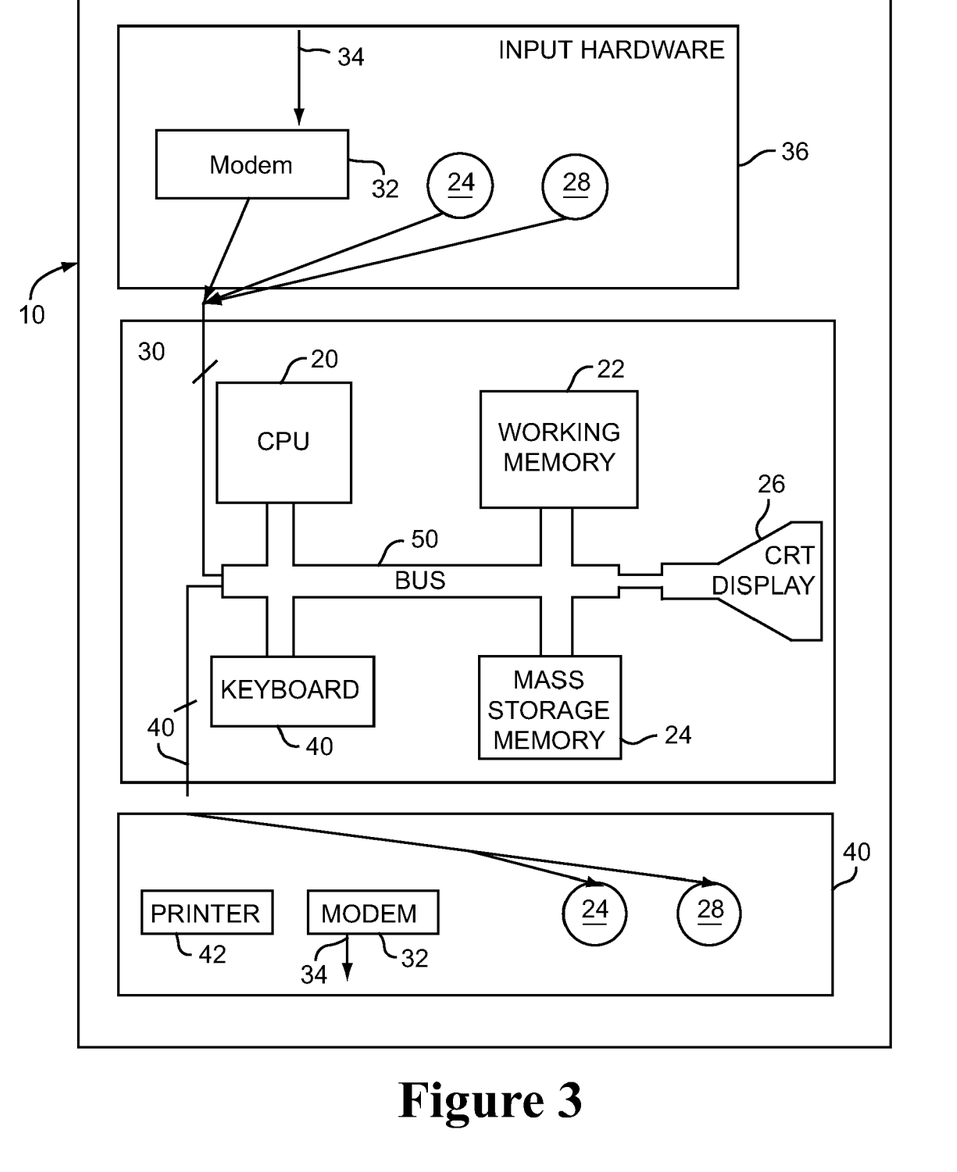
FIG. 3 is a diagrammatic representation of a system used to carry out the instructions encoded by the storage medium.
Figure 4:
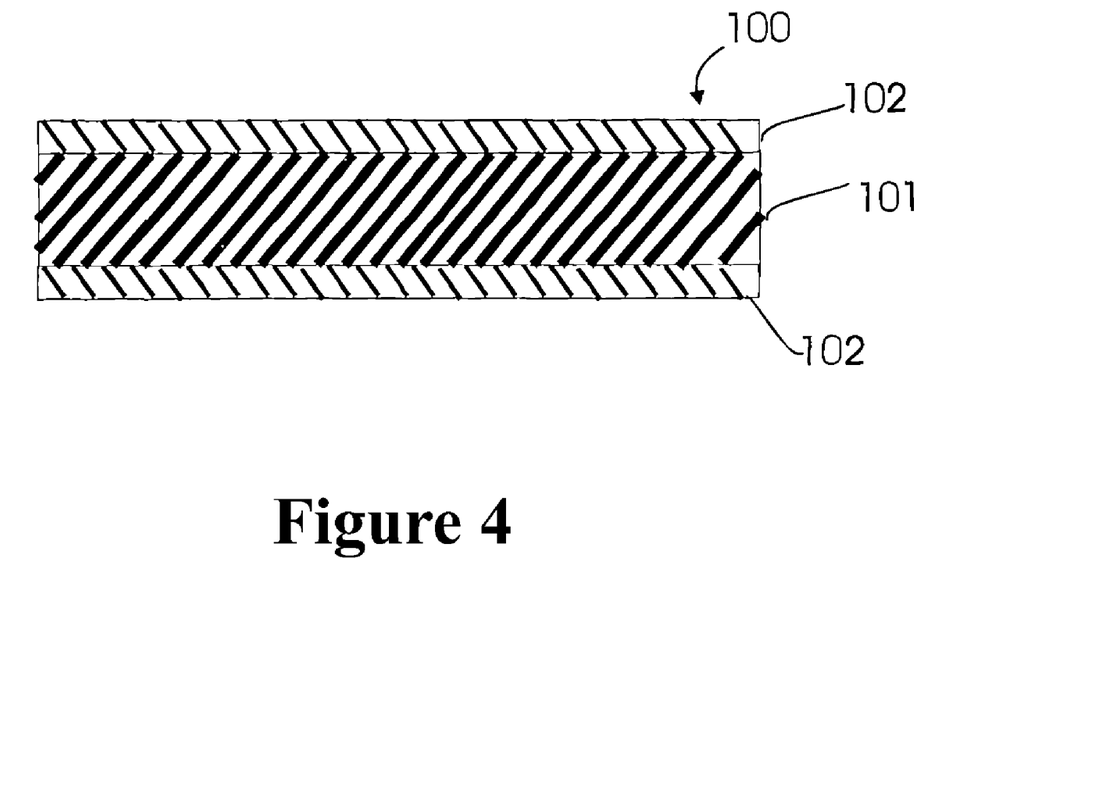
FIG. 4 is a diagrammatic representation of a cross-section of a magnetic storage medium.
Figure 5:
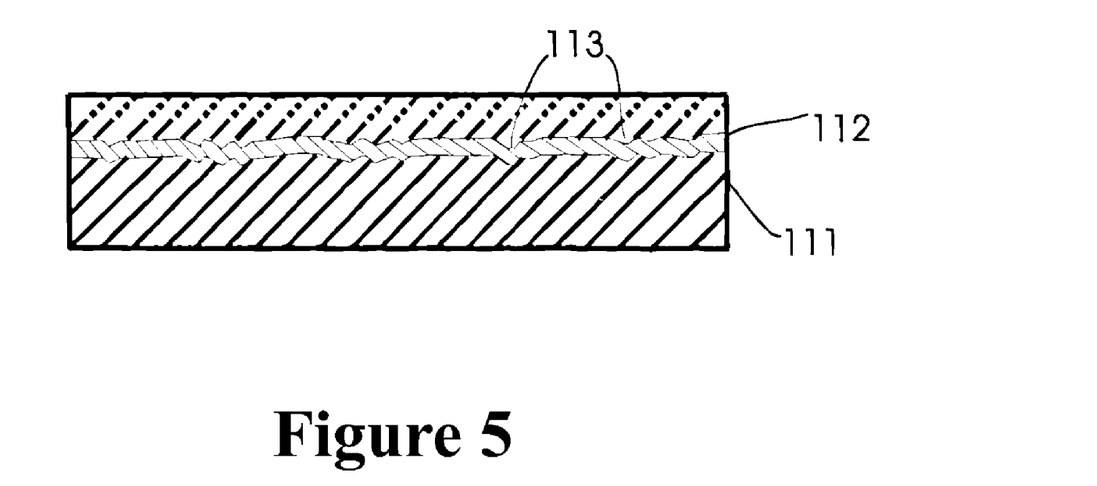
FIG. 5 is a diagrammatic representation of a cross-section of an optically readable data storage system.

A version of these embodiments is presented in FIG. 3, which shows a system 10 including a computer 11 comprising a central processing unit ("CPU") 20, a working memory 22 which may be, e.g. RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bidirectional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD. Alternatively, ROM drives or disk drives 24 in conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a synthetic polynucleotide sequence or a synthetic polypeptide sequence as described herein. Output hardware might also include a printer 42, so that hard copy output may be produced, or a disk drive 24, to store system output for later use.

In operation, CPU 20 coordinates the use of the various input and output devices 36,46 coordinates data accesses from mass storage 24 and accesses to and from working memory 22, and determines the sequence of data processing steps. A number of programs may be used to process the machine readable data of this invention. Exemplary programs may use, for example, the following steps:—

(1) inputting input $I_f$s for at least two features associated with said compound(s), wherein said features are selected from:
  (a) the ability to exhibit resistance for reduced sensitivity to a particular compound or immunological agent;
  (b) an altered DNA polymerase from wild-type HBV;
  (c) an altered surface antigen from wild-type HBV; or
  (d) morbidity or recovery potential of a patient;
(2) adding the $I_f$s for said features to provide a $P_V$ for said compound(s); and
(3) outputting said $P_V$.

FIG. 4 shows a cross section of a magnetic data storage medium 100 which can be encoded with machine readable data, or set of instructions, for designing a synthetic molecule of the invention, which can be carried out by a system such as system 10 of FIG. 3. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24. The magnetic domains of coating 102 of medium 100 are polarised or oriented so as to encode in manner which may be conventional, machine readable data such as that described herein, for execution by a system such as system 10 of FIG. 3.

FIG. 5 shows a cross section of an optically readable data storage medium 110 which also can be encoded with such a machine-readable data, or set of instructions, for designing a synthetic molecule of the invention, which can be carried out by a system such as system 10 of FIG. 3. Medium 110 can be a conventional compact disk read only memory (CD-ROM) or a rewritable medium such as a magneto-optical disk, which is optically readable and magneto-optically writable. Medium 100 preferably has a suitable substrate 111, which may be conventional, and a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which preferably is substantially transparent, is provided on top of coating 112.

In the case of a magneto-optical disk, as is well known, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

The present invention is further described by the following non-limiting Examples.

EXAMPLE 1

Patients and Treatment

Eight patients who received allogeneic BMT at the Bone Marrow Transplant Center at Queen Mary Hospital, Hong Kong were studied. They were all treated with FAM for prophylaxis against post-BMT HBV reactivation, as previously reported (23). Briefly, all patients received oral FAM 250 mg three times daily for at least one week (range: 1-12 week) before BMT and then continued for 24 weeks after BMT. FAM levels were increased to 500 mg three times daily in patients presenting with either elevated HBV DNA levels or the initial detection of HBsAg as a marker of HBV reactivation. Two patients were treated with FAM and/or LAM after liver transplantation.

Hepatitis serology and serum HBV DNA quantitation assay, hepatitis B serological markers, including HBsAg, anti-HBs, HBeAg, anti-HBe, anti-hepatitis C virus (HCV; by ETA IT), anti-hepatitis D virus and anti-HTV, were tested by commercially available enzyme immunoassays (Abbott Laboratories, Chicago, Ill., USA). Total hepatitis B core antibody (anti-HbC) was tested by radioimmunoassay (Corab, Abbott Laboratories, Chicago, Ill., USA). Serum HBV DNA was quantitated by the bDNA signal amplification assay (bDNA Quantiplex TM HBV DNA, Chiron, Emeryville, Calif., USA). Serial samples from the same patient were tested wdthin a single run to minimize interassay variation.

EXAMPLE 2

Extraction of HB VDNA from Patient Serum

Sera from 10 patients at several time points was collected and the HBV DNA extracted. Aliquots of 50 μl of the sera were mixed with 150 μl TE (10 mmol/L Tris-HCl (pH 7.5), 2 mmol/l EDTA), 1% w/v sodium dodecyl sulfate and 1 mg/ml proteinase K and incubated at 55° C. for 30 ruins. DNA was deproteinized by phenol/chloroform, precipitated with isopropanol and dissolved in 40 μl nuclease-free water.

EXAMPLE 3

PCR Amplification

The catalytic domain of the polymerase protein and the "a" determinant of the surface protein were amplified. The first round sense primer (5'GCC TCA TTT T GTG GGT CAC CAT A-3'[SEQ ID NO:1]) and the antisense primer (5'-TCT CTG ACA TAC TTT CCA AT-3' [SEQ ID NO:2]) were used in the amplification (Bresatec, Adelaide, Australia). Each reaction was carried out using 5 μl of the extracted DNA as template, 1.5 U of Tag polymerase (Perkin Elmer Cetus, Norwalk, Conn.), 1 μmol/l of sense and antisense primers, 200 μmol/l Tris-HCl (pH 8.3) and 0.01% w/v gelatin. PCR was performed by 40 cycles of denaturation (94° C. for 45 sec), annealing (55° C. for 45 sec) and extension (72° C. for 1.5 min), followed by a final extension of 7 min (Perkin-Elmer 2400, Cetus, Norwalk, Conn.). A further hemi-nested round of amplification was performed if required, using 2 μl of first round product as template and primer 5' CAC AAC AAT CCA CCA AGC T3' [SEQ ID NO:3] as the sense primer. The amplification conditions were the same as the initial round of amplification, with only 25 rounds of cycling.

EXAMPLE 4

Sequencing of the Polymerase/Envelope Genes of HBV DNA

Amplified products were gel purified using Geneclean II (BIO 101 Inc., La Mia, Calif.) and were directly sequenced using the ABI Prism Big Dye Terminator Cycle Sequencing Ready Reaction Kit according to the Manufacturer's specifications (Perkin Elmer, Cetus Norwalk, Conn.). The PCR primers were used as sequencing primers as well as several additional primers (5'-AAA TTC GCA GTC CCC AAC-3 [SEQ ID NO:4]', 5'-TCT CTG ACA TAC TTT CCA AT-3'

[SEQ ID NO:5] and 5'-GAT TCC CTC CTG TTG CTG T-3' [SEQ ID NO:6]) required to sequence the internal regions of the PCR products. MacVector and Assembly LIGN (MacVector version 6.0 and Assembly LIGN, Oxford Molecular, UK) were used to analyze all automatic sequence data. The deduced amino acid sequences were compared to the individual pretreatment isolate using the subprogram clustal W and to published HBV polymerase consensus sequence and HBsAg sequences (38-40).

EXAMPLE 5

HBV Polymerase Mutations

In this study, the dominant HBV variants selected after BMT and FCV treatment were examined by sequencing of the analytic region of the polymerase gene and the "a" determinant of the HBsAg. A number of deduced amino acid changes were detected in the catalytic region of the gene encoding the HBV polymerase, however, the majority of these changes were consistent with the changes normally found within HBV genotypes. The unique HBV mutations detected during treatment are listed in Table 1. In six out of eight patients, a mutation was detected in the polymerase at amino acid 584, in which a tyrosine, or alanine, or serine/isoleucine (mixed population) was detected (Table 1). In four out of eight patients, this mutation was detected during FAM treatment and in the remaining two patients, the mutation was detected prior to treatment. This amino acid change occurred after the termination codon of HBsAg in the overlapping reading frame. The other deduced amino acid changes which were detected in isolates from multiple patients included changes at amino acid 471, 474, 485 and 499. These changes were located in the region between the A and B domains and overlaps the "a" determinant of the HBsAg. One change was detected in the B domain of the polymerase at F524F/L. No unique mutations were detected in domain C which contains the "YMDD" motif. Changes which do not affect the HBsAg and only affect the polymerase include Q471K, T474A, L478L/M, F524F/L and I533I/V (Table 1).

In two out of two liver transplantation patients, a mutation at codon 548 was detected. The S548G mutation occurred concurrently with L526M, M550V and Y472Q mutations as detected by sequencing of clones derived from PCR amplified product. A further mutation, G548S/C was detected in an HBV isolated from a patient treated with LAM.

EXAMPLE 6

HBsAg Mutations

A number of changes were detected in the gene encoding the HBsAg, however, the majority of these changes were consistent with changes in the HBV genotype. Unique mutations which alter both the HBsAg and the polymerase are listed in Table 1 and other mutations which alter the HBsAg only are listed in Table 2. The HBsAg changes detected at 133, 139, 145 and 182 are variants which axe not detected in other genotypes (39,40). In two patients, a G145R mutation was detected after BMT and FAM treatment. In one of these patients, it was detected as a mixed population containing wild-type virus and virus with a truncated HBsAg due to a termination codon. Two mutations resulting in a truncated HBsAg were detected in two other patients. These termination codons were found at amino acid 182 and 216 (Tables 1 and 2).

EXAMPLE 7

Cloning of PCR Products

The PCR products from either first or second round PCR amplification were purified using Geneclean (Bio 101 Inc., La Jolla, Calif.) and cloned into pCR script (Stratagene) according to the Manufacturer's specifications.

TABLE 1

HBV polymerase mutations and changes in the overlapping reading frame of HBsAg

| HBV polymerase mutation | Isolate | AA change in the HBsAg |
|---|---|---|
| Q471K | A-3, 4, 5; D-1, 2, 3; F-3 | no change |
| Q471N | | |
| Y472Q | SS | T118A |
| T474A | C-2; D-1, 2; E-5 | no change |
| L478L/M | E-6 | no change |
| N485H | A-3, 4, 5; B-1, 2; D-4 | N131T |
| Y487Y/STOP | C-6 | M133K/M |
| V/G/E488L | B1, 2 | M133I* |
| L493L/W | A-4 | C139C/G* |
| F524F/L | E-6 | no change |
| I533I/V | E-5 | no change |
| V537I | E-9 | W182/STOP |
| S548G | SS | no change |
| S548S/C | MS | no change |
| N/S/H584T | A-2; B-3; E-4; H-1, 2, 3, 4, 5, 6 | after HBsAg STOP |
| N/S/H584A | C-1, 3, 4, 5, 6 | |
| H584S/I | D-5 | |
| R588R/S | B-4 | after HBsAg STOP |
| I599A | F-10 | after HBsAg STOP |

*Changes which are not detected as common variants in other genotypes of HBV.

TABLE 2

Changes in the HBsAg which do not alter the HBV polymerase protein

| HBsAg | Isolate |
|---|---|
| Y225F | A3, 4, 5; D-4; F-3 |
| Q181E | C-1 |
| Q181G | C-2, 3, 4, 5 |
| Q181Q/G | C-6 |
| S210K | C1, 3, 4, 5 |
| L216STOP | C1, C6 |
| L216L/STOP | C, 3, 4, 5 |
| S117T | E-9 |
| L175L/S | E-6 |

BIBLIOGRAPHY

1. Summers, J. and Mason, W. *Cell* 29: 403-415, 1982.
2. Vere Hodge, R. A. *Antiviral Chem. Chemother* 4: 67-84, 1993.
3. Boyd et al. *Antiviral Chem. Chemother* 32: 358-363, 1987.
4. Kruger et al. *Hepatology* 22: 219 A, 1994.
5. Main et al. *J. Viral Hepatitis* 3: 211-215, 1996.
6. Severini et al. *Antimicrobiol. Agents Chemother* 39: 1430-1435.
7. Dienstag et al. *New England J. Med,* 333: 1657-1661, 1995.
8. Lau et al. *Bone Marrow Transplant* 19: 795-9, 1997.
9. Reed et al. *Blood* 77: 195-200, 1991.
10. Pariente et al. *Dig Dis Sci* 33: 1185-91, 1988.
11. Liang et al. *J. Clin. Oncol* 1999 (in press).
12. Chen et al. *Transplantation* 49: 708-13, 1990.
13. Han et al. *Gastroenterology* 104: 1818-21, 1993.
14. Lok et al. *Ann. Intern. Med.* 116: 957, 1992.

15. Ustun et al. *Hepatology* 25: 1497-1501, 1997.
16. Lau et al. *Hepatology* 25: 1497-1501, 1997.
17. Lau et al. *J. Infect. Dis.* 178: 1585-91, 1998.
18. Shaw et al. *Antimicrob. Agents Chemother* 38: 719-23, 1994.
19. Bartholomeusz et al. *Intendrology* 40: 337-42, 1997.
20. Tsiquaye et al. *J. Med. Virol* 42: 306-10, 1994.
21. Trepo et al. *J. Hepatol* 26(1): 74, 1997.
22. Main et al. *Viral Hepat.* 3: 211-5, 1996.
23. Lau et al. *J. Hepatol.* 28: 359-68, 1998.
24. Lau et al. *Hepatology* 28: 590 A, 1998.
25. Kruger et al. *Liver Transpl. Surg.* 2: 253-62, 1996.
26. Singh et al. *Transplantation* 63: 1415-9, 1997.
27. Haller et al. *Transpl. Int.* 9(1): S210-2, 1996.
28. Boker et al. *Transplanation* 27757: 1706-8, 1994
29. Lau et al. *Hepatology* 29: 580 A, 1998.
30. Aye et al. *J. Hepatol.* 26: 1148-53, 1997.
31. Narrmov, N. V. *J. Hepatol.* 24: 282A, 1996.
32. Pichoud et al. *Hepatology* 29: 230-37,
33. Locarnini et al. *Hepatology* 29: 230-37, 1999.
34. Protzer-Knoll et al. *Hepatology* 27: 254-63, 1998.
35. Locarnini et al. *Hepatology* 26: 368 A, 1997.
36. De Man et al. *Hepatol.* 29: 669-75, 1998.
37. Voch et al. *EMBO J* 8: 3867-3874, 1989.
38. Bartholomeusz et al. *International Antiviral News* 5: 123-124, 1997.
39. Nordex et al. *J Gen Virol* 74: 1341-1348, 1993.
40. Norder et al. *Virology* 198: 489-503, 1994.
41. Lesburg et al. *Nature* 6: 937-943, 1999.

---

The invention claimed is:

1. An isolated HBV variant comprising a mutation in its DNA polymerase gene that results in a S548C substitution in its DNA polymerase, wherein the site of said substitution corresponds to position 548 of the sequence set forth in FIG. 2 (SEQ ID NO:7).

2. The HBV variant of claim 1 wherein the variant further comprises a mutation in the HBV DNA polymerase gene that results in a substitution in its DNA polymerase selected from one or more of Q471K, Q471N, Y472Q, T474A, L478M, N485H, Y487STOP, V/G/E488L, L493W, F524L, I533V, V537I, N/S/H584T, N/S/H584A, H584S/I, R588S and I599A.

3. The HBV variant of claim 1 wherein the variant further comprises a mutation in the HBV envelope protein selected from one or more of T118R, N131T, M133K, M133I, C139G and W182STOP, Y225F, Q181E, Q181G, S210K, L216STOP, S117T and L175S.

4. A method for determining the potential for an HBV to exhibit reduced sensitivity to a nucleoside analogue, said method comprising isolating DNA or corresponding mRNA from said HBV and screening for a mutation in the nucleotide sequence encoding HBV DNA polymerase resulting in a S548C substitution in its DNA polymerase, wherein the site of said substitution corresponds to position 548 of the sequence set forth in FIG. 2 (SEQ ID NO:7), and wherein the presence of such a mutation is an indication of the likelihood of resistance to said nucleoside analogue.

* * * * *

SEQUENCE LISTING

```
<160> NUMBER OF SEQ ID NOS: 8

<210> SEQ ID NO 1
<211> LENGTH: 23
<212> TYPE: DNA
<213> ORGANISM: hepatitis B virus

<400> SEQUENCE: 1
gcctcatttt gtgggtcacc ata                                               23

<210> SEQ ID NO 2
<211> LENGTH: 20
<212> TYPE: DNA
<213> ORGANISM: hepatitis B virus

<400> SEQUENCE: 2
tctctgacat actttccaat                                                   20

<210> SEQ ID NO 3
<211> LENGTH: 19
<212> TYPE: DNA
<213> ORGANISM: hepatitis B virus

<400> SEQUENCE: 3
cacaacaatc caccaagct                                                    19

<210> SEQ ID NO 4
<211> LENGTH: 18
<212> TYPE: DNA
<213> ORGANISM: hepatitis B virus

<400> SEQUENCE: 4
aaattcgcag tccccaac                                                     18

<210> SEQ ID NO 5
<211> LENGTH: 20
<212> TYPE: DNA
<213> ORGANISM: hepatitis B virus

<400> SEQUENCE: 5
tctctgacat actttccaat                                                   20

<210> SEQ ID NO 6
<211> LENGTH: 19
<212> TYPE: DNA
<213> ORGANISM: hepatitis B virus

<400> SEQUENCE: 6
```
gattccctcc tgttgctgt                                            19

```
<210> SEQ ID NO 7
<211> LENGTH: 181
<212> TYPE: PRT
<213> ORGANISM: hepatitis B Virus
<220> FEATURE:
<221> NAME/KEY: MISC_FEATURE
<222> LOCATION: (2)..(2)
<223> OTHER INFORMATION: x = Asn or Asp
<220> FEATURE:
<221> NAME/KEY: MISC_FEATURE
<222> LOCATION: (17)..(17)
<223> OTHER INFORMATION: x = Ile or Pro
<220> FEATURE:
<221> NAME/KEY: MISC_FEATURE
<222> LOCATION: (35)..(35)
<223> OTHER INFORMATION: Xaa = Ser or Asp
<220> FEATURE:
<221> NAME/KEY: MISC_FEATURE
<222> LOCATION: (44)..(44)
<223> OTHER INFORMATION: X = Thr or Asn
<220> FEATURE:
<221> NAME/KEY: MISC_FEATURE
<222> LOCATION: (46)..(46)
<223> OTHER INFORMATION: X = Arg or Asn
<220> FEATURE:
<221> NAME/KEY: MISC_FEATURE
<222> LOCATION: (47)..(47)
<223> OTHER INFORMATION: X = Asn or Ile
<220> FEATURE:
<221> NAME/KEY: MISC_FEATURE
<222> LOCATION: (48)..(48)
<223> OTHER INFORMATION: Xaa = any amino acid
<220> FEATURE:
<221> NAME/KEY: MISC_FEATURE
<222> LOCATION: (50)..(50)
<223> OTHER INFORMATION: X = Asn or Tyr or His
<220> FEATURE:
<221> NAME/KEY: MISC_FEATURE
<222> LOCATION: (52)..(52)
<223> OTHER INFORMATION: X = His or Tyr
<220> FEATURE:
<221> NAME/KEY: MISC_FEATURE
<222> LOCATION: (53)..(53)
<223> OTHER INFORMATION: X = Gly or Arg
<220> FEATURE:
<221> NAME/KEY: MISC_FEATURE
<222> LOCATION: (54)..(54)
<223> OTHER INFORMATION: X = more than 3 different AA possible
<220> FEATURE:
<221> NAME/KEY: MISC_FEATURE
<222> LOCATION: (55)..(55)
<223> OTHER INFORMATION: X = more than 3 different AA possible
<220> FEATURE:
<221> NAME/KEY: MISC_FEATURE
<222> LOCATION: (56)..(56)
<223> OTHER INFORMATION: X = more than 3 different AA possible
<220> FEATURE:
<221> NAME/KEY: MISC_FEATURE
<222> LOCATION: (57)..(57)
<223> OTHER INFORMATION: X = Asp or Asn
<220> FEATURE:
<221> NAME/KEY: MISC_FEATURE
<222> LOCATION: (60)..(60)
<223> OTHER INFORMATION: X = Asp or Asn
<220> FEATURE:
<221> NAME/KEY: MISC_FEATURE
<222> LOCATION: (61)..(61)
<223> OTHER INFORMATION: X = Ser or Tyr
<220> FEATURE:
<221> NAME/KEY: MISC_FEATURE
<222> LOCATION: (65)..(65)
<223> OTHER INFORMATION: X = Asn or Gln
<220> FEATURE:
<221> NAME/KEY: MISC_FEATURE
<222> LOCATION: (71)..(71)
<223> OTHER INFORMATION: X = Leu or Met
```

-continued

```
<220> FEATURE:
<221> NAME/KEY: MISC_FEATURE
<222> LOCATION: (75)..(75)
<223> OTHER INFORMATION: X = Lys or Gln
<220> FEATURE:
<221> NAME/KEY: MISC_FEATURE
<222> LOCATION: (77)..(77)
<223> OTHER INFORMATION: X = Tyr or Phe
<220> FEATURE:
<221> NAME/KEY: MISC_FEATURE
<222> LOCATION: (79)..(79)
<223> OTHER INFORMATION: X = Arg or Trp
<220> FEATURE:
<221> NAME/KEY: MISC_FEATURE
<222> LOCATION: (84)..(84)
<223> OTHER INFORMATION: X = Tyr or Leu
<220> FEATURE:
<221> NAME/KEY: MISC_FEATURE
<222> LOCATION: (85)..(85)
<223> OTHER INFORMATION: X = Ser or Ala
<220> FEATURE:
<221> NAME/KEY: MISC_FEATURE
<222> LOCATION: (89)..(89)
<223> OTHER INFORMATION: X = Ile or Val
<220> FEATURE:
<221> NAME/KEY: MISC_FEATURE
<222> LOCATION: (95)..(95)
<223> OTHER INFORMATION: X = Ile or Leu
<220> FEATURE:
<221> NAME/KEY: MISC_FEATURE
<222> LOCATION: (95)..(95)
<223> OTHER INFORMATION: X = Ile or Leu
<220> FEATURE:
<221> NAME/KEY: MISC_FEATURE
<222> LOCATION: (99)..(99)
<223> OTHER INFORMATION: X = Val or Gly
<220> FEATURE:
<221> NAME/KEY: MISC_FEATURE
<222> LOCATION: (114)..(114)
<223> OTHER INFORMATION: X = Cys or Leu
<220> FEATURE:
<221> NAME/KEY: MISC_FEATURE
<222> LOCATION: (115)..(115)
<223> OTHER INFORMATION: X = Ala or Ser
<220> FEATURE:
<221> NAME/KEY: MISC_FEATURE
<222> LOCATION: (116)..(116)
<223> OTHER INFORMATION: X = Val or Met
<220> FEATURE:
<221> NAME/KEY: MISC_FEATURE
<222> LOCATION: (117)..(117)
<223> OTHER INFORMATION: X = Val or Thr
<220> FEATURE:
<221> NAME/KEY: MISC_FEATURE
<222> LOCATION: (118)..(118)
<223> OTHER INFORMATION: X = Arg or Cys
<220> FEATURE:
<221> NAME/KEY: MISC_FEATURE
<222> LOCATION: (122)..(122)
<223> OTHER INFORMATION: X = Phe or Pro
<220> FEATURE:
<221> NAME/KEY: MISC_FEATURE
<222> LOCATION: (125)..(125)
<223> OTHER INFORMATION: X = Leu or Val
<220> FEATURE:
<221> NAME/KEY: MISC_FEATURE
<222> LOCATION: (126)..(126)
<223> OTHER INFORMATION: X = Ala or Val
<220> FEATURE:
<221> NAME/KEY: MISC_FEATURE
<222> LOCATION: (128)..(128)
<223> OTHER INFORMATION: X = Ser or Ala
<220> FEATURE:
<221> NAME/KEY: MISC_FEATURE
<222> LOCATION: (133)..(133)
<223> OTHER INFORMATION: X = Val or Leu or Met
<220> FEATURE:
<221> NAME/KEY: MISC_FEATURE
<222> LOCATION: (138)..(138)
<223> OTHER INFORMATION: X = Lys or Arg
```

```
<220> FEATURE:
<221> NAME/KEY: MISC_FEATURE
<222> LOCATION: (139)..(139)
<223> OTHER INFORMATION: X = Ser or Thr
<220> FEATURE:
<221> NAME/KEY: MISC_FEATURE
<222> LOCATION: (140)..(140)
<223> OTHER INFORMATION: X = Val or Gly
<220> FEATURE:
<221> NAME/KEY: MISC_FEATURE
<222> LOCATION: (29)..(29)
<223> OTHER INFORMATION: X = Ile or Val
<220> FEATURE:
<221> NAME/KEY: MISC_FEATURE
<222> LOCATION: (141)..(141)
<223> OTHER INFORMATION: X = Gln or Glu
<220> FEATURE:
<221> NAME/KEY: MISC_FEATURE
<222> LOCATION: (143)..(143)
<223> OTHER INFORMATION: X = Leu or Ser or Arg
<220> FEATURE:
<221> NAME/KEY: MISC_FEATURE
<222> LOCATION: (145)..(145)
<223> OTHER INFORMATION: X = Ser or Phe
<220> FEATURE:
<221> NAME/KEY: MISC_FEATURE
<222> LOCATION: (147)..(147)
<223> OTHER INFORMATION: X = Phe or Tyr
<220> FEATURE:
<221> NAME/KEY: MISC_FEATURE
<222> LOCATION: (148)..(148)
<223> OTHER INFORMATION: X = Thr or Ala
<220> FEATURE:
<221> NAME/KEY: MISC_FEATURE
<222> LOCATION: (149)..(149)
<223> OTHER INFORMATION: X = Ala or Ser
<220> FEATURE:
<221> NAME/KEY: MISC_FEATURE
<222> LOCATION: (150)..(150)
<223> OTHER INFORMATION: X = Val or Ile
<220> FEATURE:
<221> NAME/KEY: MISC_FEATURE
<222> LOCATION: (151)..(151)
<223> OTHER INFORMATION: X = Thr or Cys
<220> FEATURE:
<221> NAME/KEY: MISC_FEATURE
<222> LOCATION: (152)..(152)
<223> OTHER INFORMATION: X = Asn or Ser
<220> FEATURE:
<221> NAME/KEY: MISC_FEATURE
<222> LOCATION: (153)..(153)
<223> OTHER INFORMATION: X = Phe or Val
<220> FEATURE:
<221> NAME/KEY: MISC_FEATURE
<222> LOCATION: (156)..(156)
<223> OTHER INFORMATION: X = Ser or Asp
<220> FEATURE:
<221> NAME/KEY: MISC_FEATURE
<222> LOCATION: (157)..(157)
<223> OTHER INFORMATION: X = Leu or Val
<220> FEATURE:
<221> NAME/KEY: MISC_FEATURE
<222> LOCATION: (164)..(164)
<223> OTHER INFORMATION: X = Asn or Gln
<220> FEATURE:
<221> NAME/KEY: MISC_FEATURE
<222> LOCATION: (179)..(179)
<223> OTHER INFORMATION: X = Val or Ile

<400> SEQUENCE: 7

Ser Xaa Leu Ser Trp Leu Ser Leu Asp Val Ser Ala Ala Phe Tyr His
1               5                   10                  15

Xaa Pro Leu His Pro Ala Ala Met Pro His Leu Leu Xaa Gly Ser Ser
            20                  25                  30

Gly Leu Xaa Arg Tyr Val Ala Arg Leu Ser Ser Xaa Ser Xaa Xaa Xaa
        35                  40                  45
```

```
Asn Xaa Gln Xaa Xaa Xaa Xaa Xaa Leu His Xaa Xaa Cys Ser Arg
    50                  55                  60

Xaa Leu Tyr Val Ser Leu Xaa Leu Leu Tyr Xaa Thr Xaa Gly Xaa Lys
 65                  70                  75                  80

Leu His Leu Xaa Xaa His Pro Ile Xaa Leu Gly Phe Arg Lys Xaa Pro
                 85                  90                  95

Met Gly Xaa Gly Leu Ser Pro Phe Leu Leu Ala Gln Phe Thr Ser Ala
             100                 105                 110

Ile Xaa Xaa Xaa Xaa Xaa Arg Ala Phe Xaa His Cys Xaa Xaa Phe Xaa
         115                 120                 125

Tyr Met Asp Asp Xaa Val Leu Gly Ala Xaa Xaa Xaa Xaa His Xaa Glu
             130                 135                 140

Xaa Leu Xaa Xaa Xaa Xaa Xaa Xaa Leu Leu Xaa Xaa Gly Ile His
145                 150                 155                 160

Leu Asn Pro Xaa Lys Thr Lys Arg Trp Gly Tyr Ser Leu Asn Phe Met
             165                 170                 175

Gly Tyr Xaa Ile Gly
         180

<210> SEQ ID NO 8
<211> LENGTH: 76
<212> TYPE: PRT
<213> ORGANISM: Unknown
<220> FEATURE:
<223> OTHER INFORMATION: HBV variant
<220> FEATURE:
<221> NAME/KEY: MISC_FEATURE
<222> LOCATION: (2)..(2)
<223> OTHER INFORMATION: Xaa = L, or R, or I
<220> FEATURE:
<221> NAME/KEY: MISC_FEATURE
<222> LOCATION: (3)..(3)
<223> OTHER INFORMATION: Xaa = E, or D
<220> FEATURE:
<221> NAME/KEY: MISC_FEATURE
<222> LOCATION: (9)..(9)
<223> OTHER INFORMATION: Xaa = T, or D, or A, or N, or Y
<220> FEATURE:
<221> NAME/KEY: MISC_FEATURE
<222> LOCATION: (10)..(10)
<223> OTHER INFORMATION: Xaa = E, or D
<220> FEATURE:
<221> NAME/KEY: MISC_FEATURE
<222> LOCATION: (13)..(13)
<223> OTHER INFORMATION: Xaa = E, or K, or Q
<220> FEATURE:
<221> NAME/KEY: MISC_FEATURE
<222> LOCATION: (15)..(15)
<223> OTHER INFORMATION: Xaa = H, or R, or N
<220> FEATURE:
<221> NAME/KEY: MISC_FEATURE
<222> LOCATION: (18)..(18)
<223> OTHER INFORMATION: Xaa = I, or T
<220> FEATURE:
<221> NAME/KEY: MISC_FEATURE
<222> LOCATION: (23)..(23)
<223> OTHER INFORMATION: Xaa = A, or S
<220> FEATURE:
<221> NAME/KEY: MISC_FEATURE
<222> LOCATION: (26)..(26)
<223> OTHER INFORMATION: Xaa = T, or R
<220> FEATURE:
<221> NAME/KEY: MISC_FEATURE
<222> LOCATION: (40)..(40)
<223> OTHER INFORMATION: Xaa = A, or T, or S
<220> FEATURE:
<221> NAME/KEY: MISC_FEATURE
<222> LOCATION: (43)..(43)
<223> OTHER INFORMATION: Xaa = R, or T
<220> FEATURE:
<221> NAME/KEY: MISC_FEATURE
```

```
<222> LOCATION: (45)..(45)
<223> OTHER INFORMATION: Xaa = V, or G
<220> FEATURE:
<221> NAME/KEY: MISC_FEATURE
<222> LOCATION: (55)..(55)
<223> OTHER INFORMATION: Xaa = S, or I, or T, or N, or V
<220> FEATURE:
<221> NAME/KEY: MISC_FEATURE
<222> LOCATION: (56)..(56)
<223> OTHER INFORMATION: Xaa = T, or S, or H, or Y
<220> FEATURE:
<221> NAME/KEY: MISC_FEATURE
<222> LOCATION: (57)..(57)
<223> OTHER INFORMATION: Xaa = R, or H, or K, or Q
<220> FEATURE:
<221> NAME/KEY: MISC_FEATURE
<222> LOCATION: (69)..(69)
<223> OTHER INFORMATION: Xaa = Q, or P

<400> SEQUENCE: 8

Leu Xaa Xaa Asp Trp Gly Pro Cys Xaa Xaa His Gly Xaa His Xaa Ile
1               5                   10                  15

Arg Xaa Pro Arg Thr Pro Xaa Arg Val Xaa Gly Gly Val Phe Leu Val
            20                  25                  30

Asp Lys Asn Pro His Asn Thr Xaa Glu Ser Xaa Leu Xaa Val Asp Phe
        35                  40                  45

Ser Gln Phe Ser Arg Gly Xaa Xaa Xaa Val Ser Trp Pro Lys Phe Ala
    50                  55                  60

Val Pro Asn Leu Xaa Ser Leu Thr Asn Leu Leu Ser
65              70                  75
```